US010351533B2

(12) United States Patent
Schöne et al.

(10) Patent No.: US 10,351,533 B2
(45) Date of Patent: Jul. 16, 2019

(54) PROCESS FOR THE PREPARATION OF CARBAMOYLAMINO PYRAZOLE DERIVATIVES

(71) Applicant: Sandoz AG, Basel (CH)

(72) Inventors: Olga Schöne, Kundl (AT); Hans-Peter Spitzenstätter, Kundl (AT); Marius Kaufmann, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 15/738,016

(22) PCT Filed: Jun. 28, 2016

(86) PCT No.: PCT/EP2016/064922
§ 371 (c)(1),
(2) Date: Dec. 19, 2017

(87) PCT Pub. No.: WO2017/001364
PCT Pub. Date: Jan. 5, 2017

(65) Prior Publication Data
US 2018/0305319 A1  Oct. 25, 2018

(30) Foreign Application Priority Data

Jun. 29, 2015  (EP) ................................. 15174198

(51) Int. Cl.
*C07D 231/40* (2006.01)
*C07D 501/46* (2006.01)

(52) U.S. Cl.
CPC ......... *C07D 231/40* (2013.01); *C07D 501/46* (2013.01)

(58) Field of Classification Search
CPC .................................................. C07D 231/40
See application file for complete search history.

(56) References Cited

U.S. PATENT DOCUMENTS 5,201,938 A   4/1993   Costales et al.

FOREIGN PATENT DOCUMENTS

WO   2004039814 A1   5/2004
WO   2014152763 A1   9/2014

OTHER PUBLICATIONS

International Search Report and Written Opinion for PCT/EP2016/064922, dated Aug. 26, 2016.
Peng, Liu et al. Highly Efficient Synothesis of Ureas & Carbamates from Amidesby Iodosylbenzene-Induced Hoffman Rearrangement. EurJOC Journal of Organic Chemistry 2012, 1994-2000. (7 pages).
Chien T.C. et al. Facile Synthesis of 1-Substituted 4,5-Diaminopyrazoles and its application toward the Synthesis of Pyrazolo. Department of Chemistry College of Literature Science and Arts, the University of Michigan, Ann Arbor, MI 48109-1065. USA Received Feb. 24, 2004, revised Mar. 22, 2004. Published by Elsevier Ltd. (4 pages).
Xiaohui Du et al, ACS Medicinal Chemistry Letters, C5-Alkyl 2-methylurea-Substituted Pyridines as a New Class of Glucokinase Activators Published Nov. 22, 2014.
Ayako Toda et al, Bioorganic & Medicinal Chemistry Letters Synthesis and SAR of novel parenteral ani-pseudomonal cephalosporins: Discovery of FR264205 2008.
Henry E. Baumgarten et al, J. Org. Chem, vol. 40, No. 24, 1975 Reactions of Amines, XVIII the Oxidative Rearrangement of Amides with Lead Teraacetate received Jul. 17, 1974.
V.M. Vinogradov et al, Russian Chemical Bulletin, vol. 42, No. 9, Sep. 1993 5* Synthesis of substituted 3-nitropyrazoles from 3-amino-4-cynapyrazole Sep. 1993.
Dirk Landsberg et al, Synlett 2010, No.7 Synthesis of Symmetrical Ureas by (Diacetoxyiodo) benzene-Induced Hofmann Rearrangement Received Jan. 22, 2010.
Hao Song et al. Synthetic Communications Preparation of Alkyl Carbamate of 1-Protected Indole-3-methylamine as a Precursor of Indole-3-methylamine Published online Aug. 22, 2006.

*Primary Examiner* — Shawquia Jackson
(74) *Attorney, Agent, or Firm* — Luedeka Neely Group, P.C.

(57) ABSTRACT

The present invention relates to a process for the preparation of carbamoylamino pyrazole derivatives using diacetoxy-iodobenzene (PhI(OAc)$_2$) in combination with a non-nucleophilic base.

15 Claims, No Drawings

PROCESS FOR THE PREPARATION OF CARBAMOYLAMINO PYRAZOLE DERIVATIVES

This application is a Section 371 national phase entry of PCT application PCT/EP2016/064922, filed Jun. 28, 2016. This application also claims the benefit of the earlier filing date of European patent application 15174198.0, filed Jun. 29, 2015.

The present invention relates to a process for the preparation of carbamoylamino pyrazole derivatives using diacetoxyiodobenzene (PhI(OAc)$_2$) in combination with a non-nucleophilic base.

Carbamoylamino pyrazole side chains are, e.g., found in cephalosporine antibiotics, such as Ceftolozane. Ceftolozane, having the systematic IUPAC name (6R,7R)-3-([3-Amino-4-(2-aminoethylcarbamoylamino)-2-methylpyrazol-1-ium-1-yl]methyl)-7-([(2Z)-2-(5-amino-1,2,4-thiadiazol-3-yl)-2-(2-carboxypropan-2-yloxyimino)acetyl]amino)-8-oxo-5-thia-1-azabicyclo[4.2.0]oct-2-ene-2-carboxylate is depicted below:

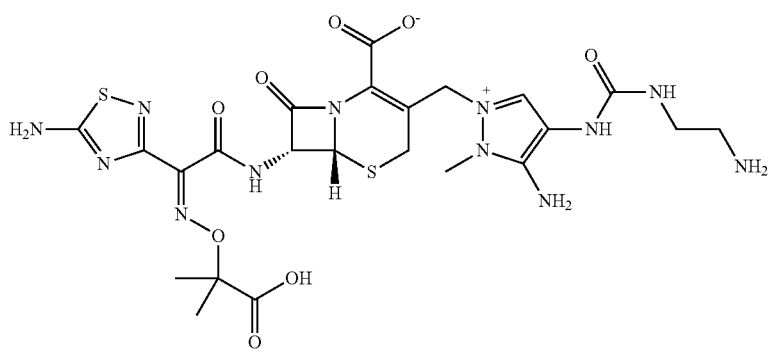

In the prior art, the carbamoylamino pyrazole side chain of Ceftolozane is made from 1-methyl-1H-pyrazole-4,5-diamine, followed by further functionalization of the 4-amino group to build up the urea moiety (WO2004/039814 and Bioorganic & Medicinal Chemistry Letters 2008, 18, 4849 which disclose slightly different conditions in some steps. A different sequence of steps 3, 4 and 5 is also disclosed in both documents which does not change the concept of the synthetic route):

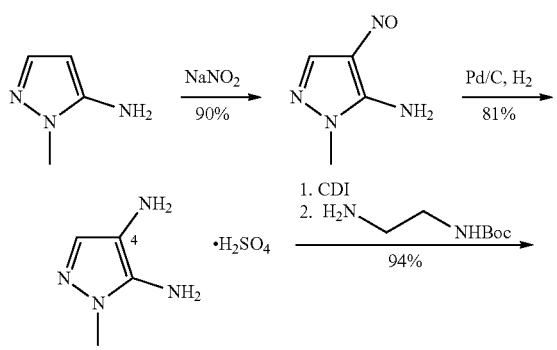

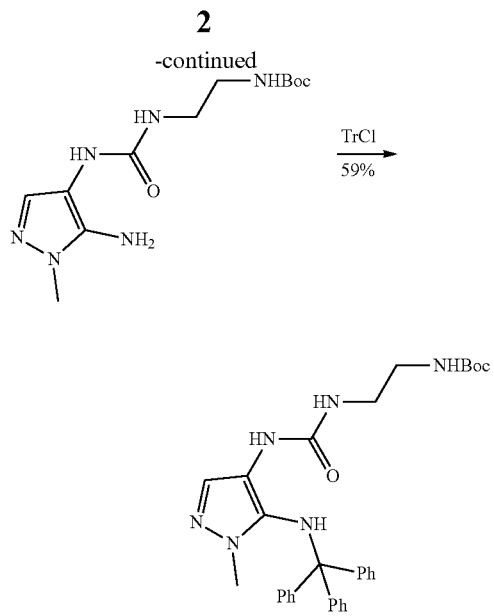

However, it is a lengthy procedure, and the synthesis of 1-methyl-1H-pyrazole-4,5-diamine requires the formation of a genotoxic and potentially explosive nitroso intermediate, followed by reduction with a transition (heavy) metal and a hazardous hydrogen atmosphere. Furthermore, the described functionalization of the 4-amino group with CDI/BocEDA was not found to be reproducible by the present inventors.

Therefore, there is a need for an improved synthesis of carbamoylamino pyrazoles such as the side chain of Ceftolozane.

All known examples in the literature to the key building block 1H-pyrazole-4,5-diamine derivative involve the reduction of nitro or nitroso intermediates as shown:

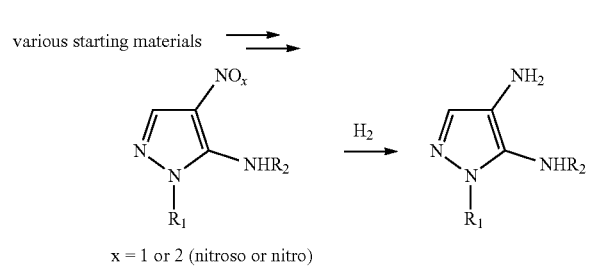

x = 1 or 2 (nitroso or nitro)

Only one conceptually different approach to pyrazole-4,5-diamine derivatives has been disclosed, which is based on the Curtius rearrangement of the corresponding ester via an acyl azide intermediate (Tetrahedron Letters, 2004, 45, 4105). However, it is also a lengthy sequence of steps with an unstable acyl azide intermediate, and no yields are given:

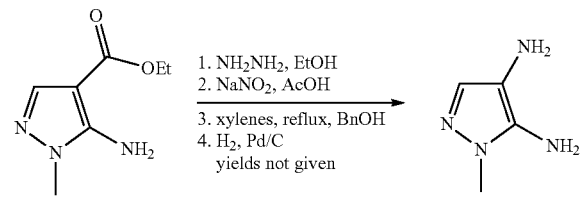

A different approach to 1H-pyrazole-4,5-diamine derivatives might involve a Hofmann rearrangement of 5-amino-1H-pyrazole-4-carboxamide derivatives:

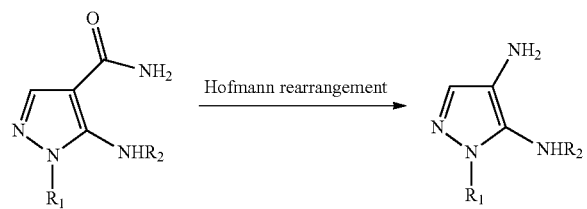

However, Hofmann rearrangements of 1H-pyrazole-4-carboxamides are generally low-yielding. U.S. Pat. No. 5,201,938A1 and Rus. Chem. Bull. 1993, 42, 1552 describe the Hofmann reaction of 1H-pyrazole-4-carboxamide derivatives with $Br_2$/NaOH to give 1H-pyrazole-4-amines in only 46% and 47% yield, respectively. The present inventors found that when tert-butyl(4-carbamoyl-1-methyl-1H-pyrazol-5-yl)carbamate is prepared and subjected to classical Hofmann reagents (NaOCl, NBS, $Br_2$), this leads to recovery of the starting material or decomposition (see comparative example 1):

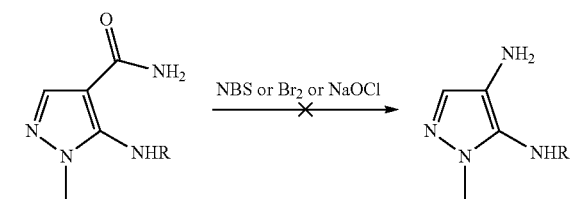

When using the milder reagent $PhI(OAc)_2$ and $KOH/H_2O$ with tert-butyl (4-carbamoyl-1-methyl-1H-pyrazol-5-yl)carbamate, the inventors of the present invention could obtain the desired 4,5-diaminopyrazole derivative, but in only 48% yield, and it could be shown that the hypervalent iodine reagent decomposes the primary amine product during the reaction (see comparative example 2):

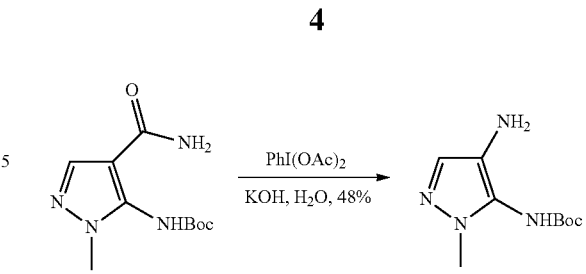

The present inventors found that the problem of aminopyrazole instability can be solved by trapping the isocyanate intermediate in situ with an alcohol to make a more stable derivative (see comparative example 3):

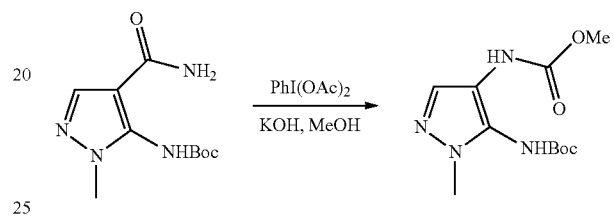

However, in the context of Ceftolozane side chain synthesis, this would introduce an extra step of carbamate deprotection, which is undesirable.

Thus, there is a need for an improved, more efficient synthesis of carbamoylamino pyrazoles, such as the side chain of Ceftolozane that among other things avoids genotoxic and explosive intermediates such as nitroso compounds and hazardous reagents such as transition metals or hydrogen gas.

It was now surprisingly found by the inventors of the present invention that 5-amino-1H-pyrazole-4-carboxamide substrates can undergo Hofmann rearrangement with $PhI(OAc)_2$ and low amounts of an amine nucleophile to directly make a stable unsymmetrical urea when used in combination with a non-nucleophilic base.

The overall synthetic sequence of the present invention is shown in an exemplary manner below:

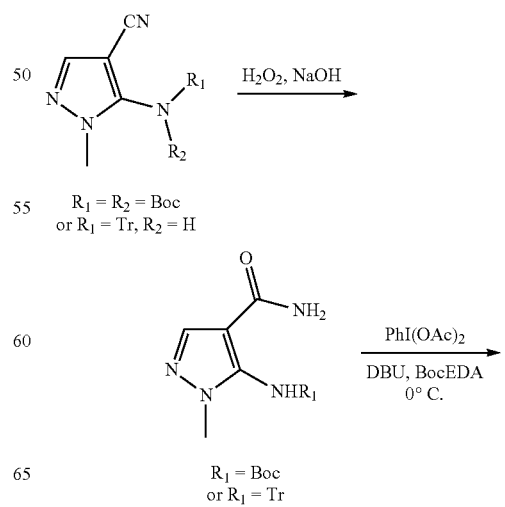

-continued

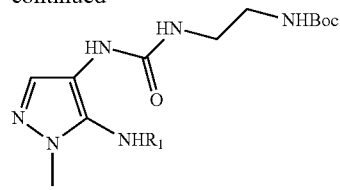

R₁ = Boc
or R₁ = Tr

Using this novel method, 5-amino-1H-pyrazole-4-carboxamide derivatives can be converted to 4-ureido-5-aminopyrazole derivatives in one pot. This method can therefore give the side chains of Ceftolozane and other cephem compounds:
a) without any nitro- or nitroso-intermediates or transition metals/hydrogen gas
b) with a shorter reaction sequence than in the process of the prior art—meaning that fewer resources, isolation and purification steps are required
Furthermore, the novel method:
c) relies on a Hofmann rearrangement with useful reagents (PhI(OAc)₂) and reagent stoichiometries (no large excess)
d) gives good yields, has proven scalability (kg-scale demonstrated) and tolerates different protecting groups on the 5-amino group
e) requires no chromatographic purification of any intermediates or the product.

The present invention thus relates to a process for production of a compound of formula

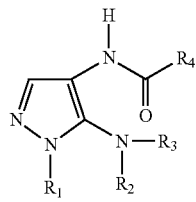

I wherein
$R_1$ is H, straight or branched $C_1$-$C_6$ alkyl, optionally substituted by 1 to 5 hydroxy groups which may be protected or halogen atoms,
$R_2$ is H, straight or branched $C_1$-$C_6$ alkyl or an amino protecting group, or $R_1$ and $R_2$ are bonded together to form $C_1$-$C_6$ alkylene or $C_2$-$C_6$ alkenylene,
$R_3$ is H, straight or branched $C_1$-$C_6$ alkyl or an amino protecting group, wherein $R_3$ is not H if $R_2$ is H,
$R_4$ is

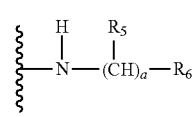

wherein
a is 0, 1, 2, 3, 4, 5 or 6,
$R_5$ is H or hydroxy which may be protected, and
$R_6$ is H, $C_1$-$C_6$ straight or branched alkyl, mono or di straight or branched $C_1$-$C_6$ alkylamino, $C_3$-$C_6$ cycloalkyl, $C_3$-$C_6$ cycloalkyl amino, $C_6$-$C_{12}$ aryl or $C_6$-$C_{12}$ aryl amino, protected amino, protected guanidino or a saturated 3- to 8-membered heterocyclic group containing 1 to 4 nitrogen atoms, wherein the cycloalkyl or aryl is optionally substituted by one or more $C_1$-$C_3$ straight or branched alkyl and the heterocyclic group is optionally substituted by one or more protected amino groups
comprising reacting the compound of formula

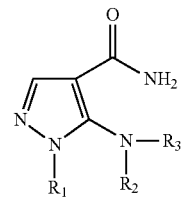

II wherein $R_1$, $R_2$ and $R_3$ are as defined above
with a compound of formula

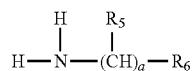

wherein a, $R_5$ and $R_6$ are as defined above
and PhI(OAc)₂ in the presence of a non-nucleophilic base to produce the compound of formula I.

Such novel process has not been suggested considering the known process for the 4-ureido-pyrazole side chain production of Ceftolozane of the literature. It is further noted that—even in fields other than Ceftolozane (or cephem) synthesis—described methods for Hofmann urea synthesis:
a) have not involved 5-amino-1H-pyrazole-4-carboxamides to the best of the inventors' knowledge,
AND
b) involve highly toxic metals like Pb or Hg which are incompatible with a pharmaceutical process (J. Org. Chem, 1975, 40, 3554), OR
c) when employing PhI(OAc)₂ require a very large excess of the amine nucleophile (used as a solvent) which limits the methods to very simple and inexpensive amines like methylamine, and do not employ a non-nucleophilic base in the process (Synth. Comm. 2005, 35, 2735; ACS Chem. Lett. 2014, 5, 1284), OR
d) when employing PhI(OAc)₂ can only make symmetrical ureas by reacting 2 equivalents of the starting material which is not useful for the desired transformation (Eur J. Org. Chem. 2012, 1994; Synlett 2010, 1104), OR
e) when employing only a small excess of amine require the use of PhIO which is much more expensive and unstable than PhI(OAc)₂ (PhIO requires storage at −20° C., is explosive upon heating). (Eur. J. Org. Chem. 2012, 1994).

In a preferred embodiment of the present invention $R_1$ is straight or branched $C_1$-$C_6$ alkyl. Suitable straight or branched $C_1$-$C_6$ alkyl (to be used e.g. as $R_1$) include methyl, ethyl, propyl, isopropyl, butyl, isobutyl, sec-butyl, tert-butyl, pentyl, tert-pentyl and hexyl. In a more preferred embodiment, $R_1$ is straight or branched $C_1$-$C_4$ alkyl.

$R_1$ can e.g. also be straight or branched $C_1$-$C_6$ alkyl substituted by 1 to 5 hydroxy groups or halogen atoms, such as chlorine, bromine, iodine and fluorine, including hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and β-hydroxyhexyl, wherein the hydroxy group(s) may be protected in each case, fluoromethyl, difluoromethyl, trifluoromethyl, chloromethyl, bromomethyl, 2-fluoroethyl, 2,2-difluoroethyl, 2,2,2-trifluoroethyl, 2-chloroethyl, 2,2-dichloroethyl, 2,2,2-trichloroethyl, 3-fluoropropyl or 2,2,3,3,3-pentafluoropropyl. In one embodiment, $R_1$ is straight or branched $C_1$-$C_4$ alkyl substituted with one hydroxy group which may be protected. In another embodiment, $R_1$ is straight or branched $C_1$-$C_4$ alkyl substituted with 1, 2 or 3 halogen atoms.

Suitable hydroxy protecting groups are, e.g., $C_4$-$C_{20}$-tert-alkyl groups, preferably $C_4$-$C_{20}$-tert-alkyl groups which carry a tertiary carbon atom in the 1-position, such as tert-butyl, 1,1-dimethylprop-1-yl, 1,1-dimethylbutyl-1-yl, 1,1,2-trimethylprop-1-yl, 1,1-dimethylpent-1-yl, 1,1,2-trimethylbut-1-yl, 1,1,3-trimethyl-but-1-yl, 1-ethyl-1-methylbut-1-yl, 1,1-dimethylhex-1-yl and 1,1-dimethyl-2-ethylbut-1-yl; $C_3$-$C_{20}$-trialkylsilyl groups, preferably $C_3$-$C_8$-trialkylsilyl groups such as trimethylsilyl, triethylsilyl, tri-n-propylsilyl, tri-propylsilyl, tri-n-butylsilyl, dimethylethylsilyl, diethylmethylsilyl, dimethyl-n-propylsilyl, dimethyl-iso-propylsilyl, dimethyl-n-butylsilyl, and dimethyl-tert-butylsilyl; lower alkylarylsilyl groups, preferably diphenylmethylsilyl, phenyldimethylsilyl, diphenyl-t-butylsilyl; benzyl; 3,4-dimethoxybenzyl; benzyloxymethyl; β-(trimethylsilyl)ethoxymethyl; p-methoxybenzyl; allyl; allyloxycarbonyl; acyl; lower alkoxy lower alkyl groups, preferably methoxymethyl, ethoxymethyl, methoxyethoxymethyl or cyclic acetal groups, such as 2-furanyl, 2-tetrahydrofuranyl, 2-pyranyl, 2-tetrahydropyranyl, 1,3-dioxan-2-yl, 1,3-dioxan-4-yl and 1,4-dioxan-2-yl.

In a preferred embodiment of the present invention $R_2$ is an amino protecting group. The process of the present invention tolerates different protecting groups.

Suitable amino protecting groups in the present invention include e.g. an acyl group as mentioned below, an aryl lower alkylidene (e.g., benzylidene), and aryl lower alkyl such as mono-, di- or triphenyl lower alkyl (e.g., benzyl, phenethyl, benzhydryl, trityl). Protecting groups for hydroxy and amino functionalities and introduction of protecting groups and later elimination after completion of the reaction are processes known to the skilled person from, for example, "Greene's Protective Groups in Organic Synthesis" by Peter G. M. Wuts and Theodora W. Greene, $4^{th}$ Ed. 2007, published by John Wiley and Sons, Inc.

"Lower" herein means $C_1$-$C_6$, if nothing else is obvious or indicated. So, for example, lower alkyl means herein $C_1$-$C_6$ alkyl if nothing else is indicated or obvious to the skilled person; lower alkylidene means $C_1$-$C_6$ alkylidene herein, if nothing else is indicated or obvious to the skilled person.

Aryl herein, e.g., refers to phenyl or naphthyl, phenyl being more preferred.

Suitable "acyl" groups in the present invention are e.g. lower alkanoyl (e.g., formyl, acetyl, propionyl, hexanoyl, pivaloyl, etc.), mono or di or tri halo lower alkanoyl (e.g., chloroacetyl, trifluoroacetyl, etc.), lower alkoxycarbonyl (e.g., methoxycarbonyl, ethoxycarbonyl, tert-butoxycarbonyl, tert-pentyloxycarbonyl, hexyloxycarbonyl, etc.), carbamoyl, aroyl (e.g., benzoyl, toluoyl, naphthoyl, etc.), aryl lower alkanoyl (e.g., phenylacetyl, phenylpropionyl, etc.), aryloxycarbonyl (e.g., phenoxycarbonyl, naphthyloxycarbonyl, etc.), aryloxy lower alkanoyl (e.g., phenoxyacetyl, phenoxypropionyl, etc.), arylglyoxyloyl (e.g., phenylglyoxyloyl, naphthylglyoxyloyl, etc.), and aryl lower alkoxycarbonyl which is optionally substituted by e.g. 1-3 suitable substituent(s), such as nitro, halogen or lower alkyl substituents (e.g., benzyloxycarbonyl, phenethyloxycarbonyl, p-nitrobenzyloxycarbonyl, etc.).

Preferable examples of "amino protecting groups" include aryl lower alkyl and acyl, in which more preferred ones are aryl lower alkyl, lower alkanoyl and lower alkoxycarbonyl. Particularly preferred examples are mono-, di- or triphenyl ($C_1$-$C_6$) alkyl, such as triphenylmethyl (trityl, Tr) and $C_1$-$C_4$ alkanoyl. Other particularly preferred examples are $C_1$-$C_6$ alkoxycarbonyl, such as tert-butyloxycarbonyl (Boc).

Suitable $C_1$-$C_6$ alkylene formed by $R_1$ and $R_2$ when bonded together includes straight alkylene having 1 to 6, preferably 2 to 4 carbon atoms, such as methylene, ethylene, trimethylene and tetramethylene, in which a more preferred one is straight alkylene having 2 or 3 carbon atoms. Suitable $C_2$-$C_6$ alkenylene formed by $R_1$ and $R_2$ includes straight alkenylene having 2 to 6, preferably 2 to 4 carbon atoms, such as vinylene and propenylene, in which a more preferred one is straight alkenylene having 2 or 3 carbon atoms.

In a preferred embodiment of the present invention $R_3$ is H and $R_2$ is not H. $R_3$ can e.g. also be a straight or branched $C_1$-$C_6$ alkyl, such as methyl, ethyl, propyl, isopropyl, butyl, isobutyl, sec-butyl, tert-butyl, pentyl, tert-pentyl and hexyl. In one embodiment it is straight or branched $C_1$-$C_4$alkyl. It can further be an amino protecting group.

$R_4$ in the present invention is

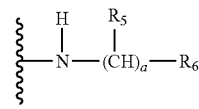

wherein
a is 0, 1, 2, 3, 4, 5 or 6. $R_5$ is (if present, i.e. if a is not 0) H or hydroxy which may be protected. If a is e.g. ≥2, then $R_5$ can be the same or different for the ≥2 (CH)$R_5$ groups. $R_6$ is H, $C_1$-$C_6$ straight or branched alkyl, mono or di straight or branched $C_1$-$C_6$ alkylamino, $C_3$-$C_6$ cycloalkyl, $C_3$-$C_6$ cycloalkyl amino, $C_6$-$C_{12}$ aryl or $C_6$-$C_{12}$ aryl amino, protected amino, protected guanidine or a saturated 3- to 8-membered heterocyclic group containing 1 to 4 nitrogen atoms, wherein the cycloalkyl or aryl is optionally substituted by one or more $C_1$-$C_3$ straight or branched alkyl and the heterocyclic group is optionally substituted by one or more protected amino groups. In one embodiment $R_6$ is H, $C_1$-$C_6$ straight or branched alkyl, mono or di straight or branched $C_1$-$C_6$ alkylamino, $C_3$-$C_6$ cycloalkyl, $C_3$-$C_6$ cycloalkyl amino, $C_6$-$C_{12}$ aryl or $C_6$-$C_{12}$ aryl amino, or protected amino, wherein the cycloalkyl or aryl is optionally substituted by one or more $C_1$-$C_3$ straight or branched alkyl.

Mono or di straight or branched $C_1$-$C_6$ alkylamino in the present invention includes as suitable examples e.g. mono or di $C_1$-$C_4$ alkylamino, methylamino, dimethylamino, ethylamino, diethylamino, N-ethyl-N-methylamino, propylamino, butylamino and N-ethyl-N-propylamino.

Suitable examples of "protected amino" include in the present invention aryl lower alkylamino and acylamino, in which more preferred ones are aryl lower alkylamino, lower alkanoylamino and lower alkoxycarbonylamino. In the present invention, protected amino is preferably mono-, di- or triphenyl $C_1$-$C_6$ alkylamino, $C_1$-$C_6$ alkanoylamino and $C_1$-$C_6$ alkoxycarbonylamino (e.g., tert-butoxycarbonylamino). Examples of "protected guanidino" include acyl-guanidino (monoacylguanidino and diacylguanidino) such as 2,3-bis (lower alkoxycarbonyl) guanidino (e.g., 2,3-bis (tert-butoxycarbonyl) guanidine), in which a more preferred one is 2,3-bis $C_1$-$C_6$ alkoxycarbonyl guanidino.

Suitable "saturated 3- to 8-membered heterocyclic group containing 1 to 4 nitrogen atoms" in the present invention includes azetidinyl (e.g., 1-azetidinyl and 3-azetidinyl), pyrrolidinyl (e.g., 1-pyrrolidinyl and 3-pyrrolidinyl), imidazolidinyl (e.g., 1-imidazolidinyl and 4-imidazolidinyl), piperidinyl (e.g., 1-piperidinyl and 4-piperidinyl) and piperazinyl (e.g., 1-piperazinyl). In one embodiment, it is a 4- to 6-membered heterocyclic group containing 1 to 4 nitrogen atoms.

In a preferred embodiment of the present invention $R_4$ is

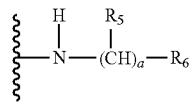

wherein
a is 0, 1, 2, 3, 4, 5 or 6,
$R_5$ is H or hydroxy which may be protected, and
$R_6$ is H, mono or di straight or branched $C_1$-$C_6$ alkylamino or straight or branched $C_1$-$C_6$ alkoxycarbonylamino.

In a more preferred embodiment of the present invention $R_4$ is

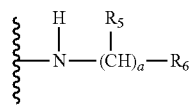

wherein
a is 1, 2, or 3,
$R_5$ is H, and
$R_6$ is straight or branched $C_1$-$C_6$ alkoxycarbonylamino.

In a particularly preferred embodiment of the present invention
$R_1$ is methyl,
$R_2$ is an amino protecting group,
$R_3$ is H, and
$R_4$ is

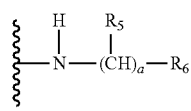

wherein a is 2,
$R_5$ is H, and
$R_6$ is protected amino.

In one embodiment of the process of the present invention
$R_1$ is methyl,
$R_2$ is Boc or trityl,
$R_3$ is H, and
$R_4$ is

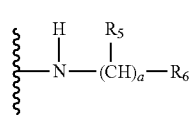

wherein a is 2,
$R_5$ is H,
and $R_6$ is NH-Boc.

In the process of the present invention the presence of a non-nucleophilic base is required for effective production of the compound of formula I. Preferably an organic non-nucleophilic base is used as the non-nucleophilic base in the present invention. More preferably a tertiary amine, such as 1,8-diazabicycloundec-7-ene (DBU), N,N-diisopropylethylamine, or triethylamine, is used as the non-nucleophilic base in the present invention. In a particularly preferred embodiment, DBU is used as the non-nucleophilic base in the present invention. Particularly good yields are obtainable in this case. Other non-nucleophilic bases that can be used as the non-nucleophilic base herein are, e.g., pyridine which is optionally substituted by 1-5 $C_1$-$C_6$ straight or branched alkyl (e.g., 2,6-di-tert-butylpyridine or 2,6-di-tert-butyl-4-methylpyridine), diisopropylethylamine (DIPEA), triethylamine or other $C_1$-$C_6$ trialkylamines, quinuclidine, tetramethyl piperidine, or trimethylguanidine. In one embodiment, 1,1,3,3-tetramethylguanidine, 1,5-Diazabicyclo[4.3.0]non-5-ene (DBN), 1,8-diazabicycloundec-7-ene (DBU), 7-Methyl-1,5,7-triazabicyclo(4.4.0)dec-5-ene (MTBD) or 1,5,7-Triazabicyclo(4.4.0)dec-5-ene (TBD) is used in the present invention as the non-nucleophilic base.

The process of the present invention for production of the compound of formula I is preferably conducted in a non-nucleophilic solvent. The non-nucleophilic solvent is different from the non-nucleophilic base.

In a particularly preferred embodiment of this invention, production of the compound of formula I is conducted in 2-methyltetrahydrofuran or in dichloromethane. Production of the compound of formula I can also e.g. be conducted in THF, 1,4-dioxane, diethyl ether, trichloromethane, dichloroethane, acetonitrile, benzene, toluene, dimethyl sulfoxide (DMSO), or dimethylformamide (DMF). The use of 2-methyltetrahydrofuran is particularly preferred if $R_2$ is Boc. The use of dichloromethane is particularly preferred if $R_2$ is trityl. For the production of formula I according to the process of the present invention, the compound of formula II is e.g. suspended in the non-aqueous medium to which the compound of formula III, the non-nucleophilic base (such as DBU) and PhI(OAc)$_2$ are added. in one embodiment PhI(OAc)$_2$ is added in 2 or more portions. Production of the compound of formula I from the compound of formula II according to the present invention e.g. takes place at an internal temperature of 0-5° C.

As production of the compound of formula I from the compound of formula II is preferably conducted in an environment with limited water content to avoid formation of the amine instead of the urea derivative, the use of starting compounds with little or no water content in the process of the present invention is advantageous. The water content in the non-nucleophilic solvent and the non-nucleophilic base is therefore preferably less than 10 wt.-% each, more preferably less than 5 wt.-% or less than 1 wt.-% each. In a further preferred embodiment of this invention, production of the compound of formula I is conducted under anhydrous conditions. Herein, the term "anhydrous" refers to a reaction mixture that includes less than 1 wt.-% water, preferably less than 0.7 wt.-% water, preferably less than 0.5 wt.-% water, or, preferably, is devoid of water. After the compound of formula I is produced, however, it is not excluded that water is used during work-up.

In this specification, "%" is on a weight by weight basis, if nothing else is explicitly stated or evident for a skilled person in the specific context.

The compounds of formula II and III are, e.g., used in a molar ratio of 1/1 to 1/4 in the present invention. In a preferred embodiment of the present invention the compounds of formula II and formula III are used in a molar ratio of 1/1.2 to 1/3. The molar ratio of the compounds of formula II and formula III is, e.g., 1/1.2 to 1/2. The molar ratio of the compounds of formula II and PhI(OAc)$_2$ is, e.g., 1/1.1 to 1/3. In another preferred embodiment of the present invention the compounds of formula II and PhI(OAc)$_2$ are used in a molar ratio of 1/1.1 to 1/1.9. Yields above 60% are obtainable with the present invention in the production of the compound of formula I from the compounds of formulae II and III.

Regarding the molar ratio of the compound of formula II and the non-nucleophilic base preferably the molar ratio of the compound of formula II and the non-nucleophilic base (such as DBU) is 1:1 or smaller, such as 1:2 to 1:10, more preferably 1:2.5 to 1:5.5, even more preferably 1:3 to 1:5 or 1:3 to 1:4 in the process of the present invention. In one embodiment, the molar ratio of the compound of formula II and the non-nucleophilic base is 1:3. More preferably, the non-nucleophilic base is DBU and the molar ratio of the compound of formula II and of DBU is 1:3.

As the formation of compound I from compounds II and III can be done as a one pot process, the process is concise, time and resource efficient. Furthermore, the process is easily scalable allowing for industrial scale production. In one embodiment, the process of the present invention is thus an industrial process. The employed amount of DBU in the process of the present invention is e.g. 1.0 kg, such as ≥1.8 kg. In one embodiment of the process of the present invention the employed amount of the compound of formula III is e.g. ≥1.0 kg, In a preferred embodiment of the present invention the compound of formula II is prepared by a process of converting a compound of formula

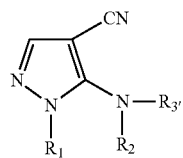

IV wherein R$_1$ and R$_2$ are as defined above, and R$_{3'}$ is straight or branched C$_1$-C$_6$ alkyl or an amino protecting group into the compound of formula II. This is preferably done by using hydrogen peroxide under basic conditions. Yields of above 80% are obtainable for this step, adding to the high efficiency of the production process of the present invention. In one embodiment in the process of converting the compound of formula IV into the compound of formula II, R$_3$ in the compound of formula II is the same as R$_{3'}$ in the compound of formula IV. In one embodiment in the process of converting the compound of formula IV into the compound of formula II R$_2$ and R$_{3'}$ in the compound of formula IV are both amino protecting groups, of which one amino protecting group is eliminated when converting the compound of formula IV into the compound of formula II (so that one of R$_2$ or R$_3$ in the compound of formula II then is H). In one embodiment of the present invention, both R$_2$ and R$_{3'}$ in the compound of formula IV are Boc and in the process of converting the compound of formula IV into the compound of formula II, one of the Boc groups is eliminated from the 5-amino group and a compound of formula II is obtained wherein R$_2$ is Boc and R$_3$ is H. In this process, e.g., ethanol is preferably used as solvent.

In another embodiment of the present invention, R$_2$ is trityl and R$_{3'}$ is H or straight or branched C$_1$-C$_6$ alkyl in the compound of formula IV, which is converted into the compound of formula II, wherein R$_2$ is trityl and R$_3$ is the same as R$_{3'}$ in the compound of formula IV. In this process, e.g., DMSO is preferably used as solvent.

In one embodiment of the present invention, the process for production of a compound of formula I comprises as a first step preparing the compound of formula IV wherein R$_2$ and/or R$_{3'}$ is an amino protecting group by introduction of the amino protecting groups(s) to the 5-amino group of the pyrazole ring of the compound of formula

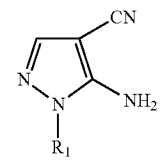

V wherein R$_1$ is as defined above. In a second step, the compound of formula IV is converted into the compound of formula II as described above. In a third step, the compound of formula I is produced from the compound of formula II as described above.

The present invention also relates to a compound of formula I

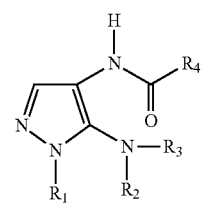

I wherein
R$_1$ is H, straight or branched C$_1$-C$_6$ alkyl, optionally substituted by 1 to 5 hydroxy groups which may be protected or halogen atoms,
R$_2$ is H, straight or branched C$_1$-C$_6$ alkyl or an amino protecting group, or R$_1$ and R$_2$ are bonded together to form C$_1$-C$_6$ alkylene or C$_2$-C$_6$ alkenylene,
R$_3$ is H, straight or branched C$_1$-C$_6$ alkyl or an amino protecting group, wherein R$_3$ is not H if R$_2$ is H,
R$_4$ is

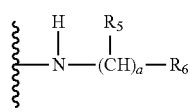

wherein
a is 0, 1, 2, 3, 4, 5 or 6,
R$_5$ is H or hydroxy which may be protected, and
R$_6$ is H, C$_1$-C$_6$ straight or branched alkyl, mono or di straight or branched C$_1$-C$_6$ alkylamino, C$_3$-C$_6$ cycloalkyl, C$_3$-C$_6$ cycloalkyl amino, C$_6$-C$_{12}$ aryl, C$_6$-C$_{12}$ aryl amino, protected amino, protected guanidino or a saturated 3- to 8-membered heterocyclic group containing 1 to 4 nitrogen atoms, wherein the cycloalkyl or aryl is optionally substituted by one or more $C_1$-$C_3$ straight or branched alkyl and the heterocyclic group is optionally substituted by one or more protected amino groups,
obtainable by a process
comprising reacting the compound of formula

II

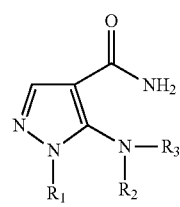

wherein $R_1$, $R_2$ and $R_3$ are as defined above with a compound of formula

III

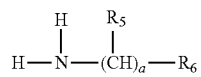

wherein a, $R_5$ and $R_6$ are as defined above
and PhI(OAc)$_2$ in the presence of a non-nucleophilic base to produce the compound of formula I.

The preferred features and embodiments of the process for production of a compound of formula I as described above also apply here. This, e.g., means that in a particularly preferred embodiment, the compound of formula I is obtainable by a process for production of the compound of formula I, wherein the non-nucleophilic base is DBU.

The process of the present invention can also include a step of deprotecting the compound of formula I if it contains protecting groups. Thus, the present invention also relates to a process for the production of a compound of formula I from a compound of formula II and a compound of formula III as described above further comprising removing one or more remaining protecting groups from the compound of formula I. It also relates to said process wherein the compound of formula II is prepared from a compound of formula IV as described above, wherein the compound of formula IV can be prepared from a compound of formula V as described above. E.g. if the 5-amino group of the pyrazole ring of the compound of formula I is protected with a protecting group, it can be deprotected in a further step. Boc deprotection is, e.g., performed by using thermal conditions (e.g. by heating (such as to >80° C.) the solution of the compound of formula I in ethanol after addition of water. Preferably no additional reagents are used during deprotection. Good yields are thus obtainable.

The present invention further relates to a process for the preparation of a cephem antibiotic or a salt thereof, which comprises
 a) preparing a compound of formula I by a process as described above, and
 b) using the compound of formula I as an intermediate for the preparation of the cephem antibiotic or the salt thereof.

In one embodiment of the process for the preparation of the cephem antibiotic or the salt thereof step b) comprises reacting the compound of formula I, optionally after deprotection, with at least one other intermediate product and removing any remaining protection group to obtain the cephem antibiotic or the salt thereof.

In one embodiment, the present invention particularly relates to a process for the preparation of Ceftolozone or a salt thereof, which comprises
 a) preparing a compound of formula I by a process as described above wherein $R_1$ is methyl, $R_2$ is H or an amino protecting group, $R_3$ is an amino protecting group, and
 $R_4$ is

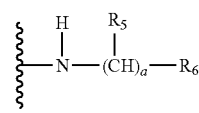

wherein a is 2,
 $R_5$ is H, and
 $R_6$ is protected amino,
 b) using the compound of formula I as an intermediate for the preparation of Ceftolozane or salt thereof.

In one embodiment of the process for the preparation of Ceftolozane or salt thereof step b) comprises reacting the compound of formula I, optionally after deprotection, with at least one other intermediate product and removing any remaining protection group to obtain Ceftolozane or the salt thereof.

For the disclosure of processes for the preparation of cephem antibiotics or salts thereof (such as Ceftolozane or a salt thereof) using a compound of formula I as an intermediate and suitable other intermediate products, it is explicitly referred to WO2004/039814 (see in particular claim 12 (3) and process 3) and WO 2014/152763 (see in particular example 1).

The present invention also relates to Ceftolozane or a salt thereof obtainable by a process which comprises
 a) preparing a compound of formula I by a process as described above wherein $R_1$ is methyl, $R_2$ is H or an amino protecting group, $R_3$ is an amino protecting group, and
 $R_4$ is

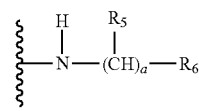

wherein a is 2,
 $R_5$ is H, and
 $R_6$ is protected amino,
 b) using the compound of formula I as an intermediate for the preparation of Ceftolozane or salt thereof.

The preferred features and embodiments of the process for production of a compound of formula I as described above also apply here. This, e.g., means that in a particularly preferred embodiment, Ceftolozane or the salt thereof is obtainable by a process for preparation of Ceftolozane or a salt thereof, wherein in step a) DBU is used as the non-nucleophilic base in the process for preparing the compound of formula I.

The following examples are illustrative without restricting the scope of protection. If in the examples and comparative examples a process detail is not explicitly described, a skilled person can easily find such detail according to the general practice in the art.

Abbreviations used herein
Ac acetate
Boc tert-butyloxycarbonyl
BocEDA N-Boc ethylenediamine, tert-butyl (2-aminoethyl)carbamate
Boc$_2$O di-tert-butyl dicarbonate
DBU 1,8-Diazabicycloundec-7-ene
DCM dichloromethane
DIPET diisopropylether
DMAP 4-dimethylamino pyridine
DMSO dimethyl sulfoxide
Et ethyl
EtOAc ethyl acetate
Equiv equivalent(s)
HPLC high pressure liquid chromatography
M molar, molarity
Me methyl
mM millimolar
MeOH methanol
Me-THF 2-methyltetrahydrofuran
NMR nuclear magnetic resonance
ppm parts per million
R any substituent
rt. room temperature
TEA triethylamine
THF tetrahydrofuran
TLC thin layer chromatography
TMS tetramethylsilane
Tr Trityl, triphenylmethyl
UV ultraviolet General Analytical Methods:

Reactions were monitored by HPLC on a C-18 reverse phase column with a gradient of acetonitrile in 10 mM ammonium sulfamate aqueous buffer at pH 5.6 or 40 mM aqueous sulfamic acid, or using thin layer chromatography (TLC) on silica gel pre-coated aluminum sheets (Silica gel 60 F$_{254}$, Merck). TLC visualization was accomplished by irradiation with UV light at 254 nm and/or a ceric ammonium molybdate stain. $^1$H and $^{13}$C chemical shifts are reported in ppm relative to TMS (0 ppm) with the solvent resonance as the internal standard (CDCl$_3$, $^1$H: 7.26 ppm, $^{13}$C: 77.16 ppm, (CD$_3$)$_2$O $^1$H: 2.05 ppm, $^{13}$C: 29.84, 202.26 ppm, DMSO: $^1$H: 2.50 ppm, $^{13}$C: 39.51 ppm).

EXAMPLE 1

Synthesis of di-tert-butyl (4-cyano-1-methyl-1H-pyrazol-5-yl)imidodicarbonate

In a 10 L reactor, 5-amino-1-methyl-1H-pyrazole-4-carbonitrile (501.95 g, 4.11 mol, 1 equiv) was suspended in 2-methyltetrahydrofuran (Me-THF, 7.5 L). To this suspension, triethylamine (828.6 g, mL, 8.19 mol, 2 equiv) and DMAP (85.0 g, 0.69 mol, 0.17 equiv) were added in one portion, keeping the inner temperature at 25° C. in a separate 6 L reactor, di-tert-butyl dicarbonate (1966 g, 9.0 mol, 2.2 equiv) was dissolved in Me-THF (2.5 L). This solution was added to the main reactor over 23 min keeping the reaction temperature ≤30° C. (caution: gas evolution). The reaction was heated to +47° C. and stirred for 4.8 h, after which HPLC control indicated complete disappearance of the starting material. The reaction was cooled to +25° C. and charged with water (2.0 L). The pH was adjusted to 3.1 with 10% aq. HCl (3257 g), and the phases separated. The aqueous phase was discarded and the organic phase charged with water (1.75 L) and sat. aq. NaCl (1.75 L). The pH was adjusted to 10.2 with 1M NaOH (813 g) and the solution stirred for 5 min. The stirring was stopped and phases separated. The aqueous phase was discarded and the organic phase charged with sat. aq. NaCl (2.5 L), stirred for 10 min and the phases separated. The aqueous phase was discarded and the organic phase was transferred to a rotary evaporator. Volatiles were removed under reduced pressure to afford the title product as a clear gum (1402 g) which slowly solidified, and was used without further purification.

Characterization Data for the Product:
$^1$H NMR (300 MHz, DMSO): 8.12 (s, 1H), 3.71 (s, 3H), 1.41 (s, 18H).

EXAMPLE 2

Synthesis of 1-methyl-5-(tritylamino)-1H-pyrazole-4-carbonitrile

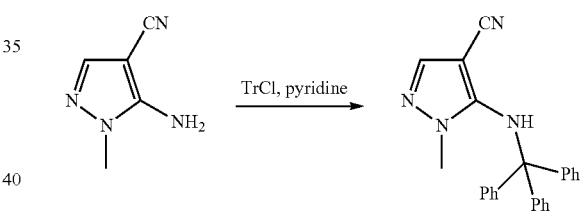

In a two-neck round bottom flask, 5-amino-1-methyl-1H-pyrazole-4-carbonitrile (970.9 g, 7.95 mmol, 1 equiv) was suspended in pyridine (10 mL). To this suspension trityl chloride (1.99 g, 7.15 mmol, 0.9 equiv) was added, and the reaction was heated to 60° C., whereby a clear solution was initially formed, followed by the gradual appearance of a precipitate. The reaction was stirred for 15 h, after which further trityl chloride (1.11 g, 3.97 mmol, 0.5 equiv) was added, followed by ethanol (2.32 mL). The reaction was stirred for 23 h, after which HPLC control indicated 94% conversion of the starting material. The reaction was charged with water (50 mL) and dichloromethane (50 mL) and pH was adjusted to 2.25 with 50% aq. H$_2$SO$_4$. The phases were separated, the organic phase charged was charged with water (50 mL) and pH was adjusted to 10 with 2M NaOH. The phases were separated, the organic phase was washed with sat. aq. NaCl (50 mL), dried over Na$_2$SO$_4$ and filtered. To the filtrate was added 100 mL diisopropylether (DIPET) and the solution was concentrated under reduced pressure to 25 g, initiating crystallization. The crystal suspension was cooled at 4° C. for 1 h and filtered, washing the filter cake with cold DIPET. Drying at 30° C. under reduced pressure for 17 h gave the title product as white crystalline solid (1.47 g, 4.0 mmol, 50%).

17

Characterization Data for the Product:

$^1$H NMR (300 MHz, DMSO): 7.46 (s, 1H), 7.37-7.16 (m, 15H), 6.77 (s, 1H), 3.53 (s, 3H).

$^{13}$C NMR (75 MHz, DMSO): 147.8, 144.7, 141.1, 128.9, 127.7, 127.5, 114.8, 81.3, 71.8, 35.6.

EXAMPLE 3

Synthesis of tert-butyl (4-carbamoyl-1-methyl-1H-pyrazol-5-yl)carbamate

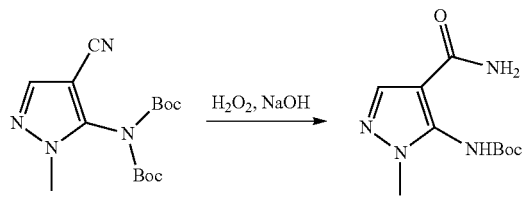

In a 30 L reactor equipped with a gas exhaust (20 L/h flow rate) and a reflux condenser, di-tert-butyl (4-cyano-1-methyl-1H-pyrazol-5-yl) imidodicarbonate prepared according to Example 1 (1349 g, 1 equiv) was dissolved in ethanol (6.8 L). To this solution, 1M NaOH (11.9 L) was added in one portion, keeping the reaction temperature at 30° C. A 35% aqueous $H_2O_2$ solution (2788 g) was then added over 120 min (caution: gas evolution) keeping the inner temperature below 40° C. The reaction was stirred for an additional 1 h, after which HPLC control indicated complete disappearance of the starting material and <1% of the mono Boc-protected intermediate tert-butyl (4-cyano-1-methyl-1H-pyrazol-5-yl)carbamate. A solution of $Na_2SO_3$ (720 g) in water (6 L) was added to the reaction mixture over 5 min, and the mixture was stirred for 17 min. The pH was adjusted to 10.7 with 10% aq. HCl (1265 g), and the crude reaction mixture extracted with EtOAc (4×15 L). The combined organic layers (70 L) were divided into 2 portions and each portion concentrated under reduced pressure to ca. 10 L, stripped with EtOAc by continuous addition of solvent and evaporation while keeping the volume at ca. 10 L and seeded, initiating crystallization. Each portion of the crystal suspension was further evaporated to an end mass of ca. 3400 g and both portions were combined and kept at −20° C. for 20 h. The crystal suspension was filtered washing the filter cake with a cold cyclohexane/EtOAc (2:1) solution. Drying at 40° C. under reduced pressure for 16 h gave the title product as white crystalline solid (882 g, 3.67 mol, 89% over 2 steps).

Characterization Data for the Product:

$^1$H NMR (300 MHz, $(CD_3)_2O$): 8.56 (br s, 1H), 7.81 (s, 1H), 7.10 (br s, 1H), 6.50 (br s, 1H), 3.77 (s, 3H), 1.50 (s, 9H).

$^{13}$C NMR (75 MHz, DMSO): 163.5, 153.0, 137.7, 137.4, 109.7, 79.9, 35.6, 27.9.

18

EXAMPLE 4

Synthesis of 1-methyl-5-(tritylamino)-1-pyrazole-4-carboxamide

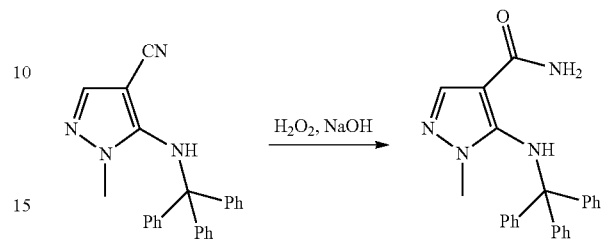

In a two-neck round bottom flask, 1-methyl-5-(tritylamino)-1H-pyrazole-4-carbonitrile prepared according to Example 2 (634.0 mg, 1.74 mmol, 1 equiv) was dissolved in DMSO (7 mL). To this solution 5 M NaOH (1.19 mL, 5.95 mmol, 3.4 equiv) was added, followed by 35% aq. $H_2O_2$ (1.4 mL, 9 equiv) dropwise (caution: reaction highly exothermic). The foaming reaction was cooled by the addition of 10 mL DMSO and stirred for 30 min, after which HPLC analysis indicated 98% conversion. The reaction was charged with water (30 mL), stirred for 30 min and filtered, washing the filter cake with water (10 mL). Drying at under reduced pressure gave the title product as white crystalline solid (560 mg, 1.46 mmol, 84%).

Characterization Data for the Product:

$^1$H NMR (300 MHz, DMSO): 8.93 (s, 1H), 7.63 (s, 1H), 7.47-7.15 (m, 16H), 6.76 (br s, 1H), 2.88 (s, 3H).

$^{13}$C NMR (75 MHz, DMSO): 166.45, 149.1, 156.6, 137.2, 128.3, 128.0, 127.0, 101.3, 71.7, 38.3.

EXAMPLE 5

Synthesis of tert-butyl (2-(3-(5-tert-butoxycarbonyl) amino-1-methyl-1H-pyrazol-4-yl)ureido)ethyl)carbamate

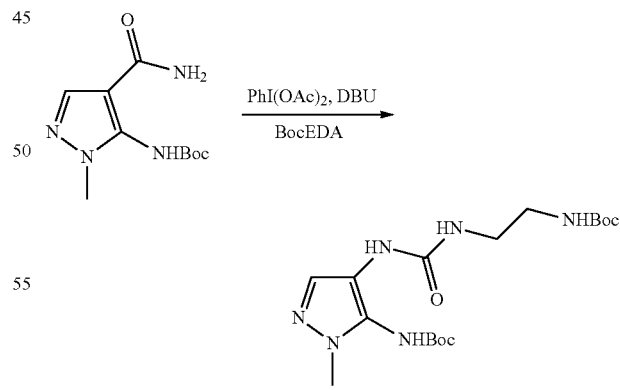

In a 20 L reactor, tert-butyl (4-carbamoyl-1-methyl-1H-pyrazol-5-yl)carbamate prepared according to Example 3 (783.4 q, 3.26 mol, 1 equiv) was suspended in Me-THF (8.3 L) and the reaction was cooled to 0° C. To this suspension, tert-butyl (2-aminoethyl)carbamate (BocEDA, 1033.5 g, 6.45 mol, 1.86 equiv) was added in one portion, followed by DBU (1768.8 g, 11.6 mol, 3.3 equiv) keeping the inner temperature at 0° C. Diacetoxyiodobenzene (665.4 g, 2.07 mol, 0.6 equiv) was added in one portion and the reaction was stirred for 68 min at 0° C. A second portion of diacetoxyiodobenzene (663.6 g, 2.06 mol, 0.6 equiv) was added and the reaction was stirred for 4 h at 0° C. The reaction was warmed up to 20° C. and charged with 17% aq. NaCl solution (7 L), stirred and the phases were separated. The organic phase was charged with 10% aq. $Na_2SO_3$ solution (4.2 L) and stirred. The pH was adjusted to 3.5 with 10% aq. HCl (2969 g) and the phases separated. The organic phase was charged with 8% aq. $NaHCO_3$ solution, stirred and the phases were separated. The organic phase was evaporated under reduced pressure to dryness, the residue was redissolved in MeOH (6.7 L) and extracted with heptane (3×6.7 L). The combined heptane phases were discarded and the methanol phase was evaporated under reduced pressure to dryness, redissolved in acetone (3.3 L) and evaporated to dryness again. The residue was taken up in acetone (5 L) and stirred for 1 h at 20° C., whereby crystallization was initiated. Cyclohexane (7.5 L) was added dropwise over 42 min and the crystal suspension was stirred for 52 min, cooled to −10° C. and stirred for further 13 h. The suspension was filtered, washing the filter cake with cold (−10° C.) solution of acetone/cyclohexane (1:3) (4 L). Drying at 40° C. under reduced pressure for 16 h gave the title product as white crystalline solid (803 g, 2.01 mol, 62%).

Characterization Data for the Product:

$^1$H NMR (300 MHz, DMSO): 8.72 (br s, 1H), 7.49 (s, 1H), 6.81 (br s, 1H), 6.34 (br s, 1H), 3.55 (s, 3H), 3.15-3.02 (m, 2H), 3.02-2.90 (m, 2H), 1.51-1.30 (m, 18H).

$^{13}$C NMR (75 MHz, DMSO): 155.6, 155.4, 153.3, 130.4, 125.0, 116.6, 79.8, 77.6, 40.5, 39.1, 35.3, 28.2, 27.9.

EXAMPLE 6

Synthesis of 4-(3-{2-[(tert-butoxycarbonyl) amino] ethyl}ureido)-1-methyl-5-triphenylmethylaminopyrazole

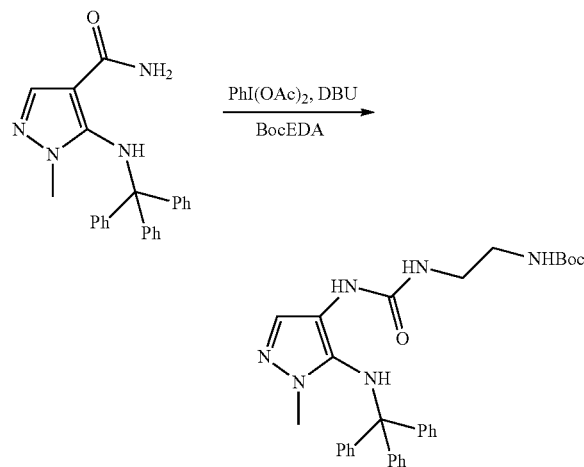

In a two-neck round bottom flask, 1-methyl-5-(tritylamino)-1H-pyrazole-4-carboxamide prepared according to Example 4 (92 mg, 0.24 mmol, 1 equiv) was suspended in dichloromethane (2.5 mL). To this suspension, tert-butyl (2-aminoethyl)carbamate (BocEDA, 97.3 mg, 0.58 mmol, 2.4 equiv) was added in one portion, followed by DBU (134 µL, 0.9 mmol, 3.7 equiv), whereby a clear solution was obtained after several minutes of stirring. The reaction was cooled to 0° C. and diacetoxyiodobenzene (105.2 mg, 0.33 mmol, 1.4 equiv) was added in one portion and the reaction was stirred for 75 min at 0° C., after which HPLC indicated complete conversion. The crude reaction mixture was evaporated under reduced pressure to dryness, the residue was redissolved in MeOH (5 mL) and extracted with heptane (4×5 mL). The combined heptane phases were discarded and the methanol phase was evaporated under reduced pressure to dryness, redissolved in dichloromethane (10 mL) and washed with 17% aq. NaCl solution (15 mL). The phases were separated, and the organic phase allowed to stand at r.t., whereby crystallization initiated. The crystal suspension was allowed to stand at −20° C. for 2 days and filtered. Drying at r.t. under reduced pressure for 2 h gave the title product as white crystalline solid (80 mg, 0.15 mmol, 62%).

Characterization Data for the Product:

$^1$H NMR (300 MHz, DMSO): 8.72 (br s, 1H), 7.49 (s, 1H), 6.81 (br s, 1H), 6.34 (br s, 1H), 3.55 (s, 3H), 3.15-3.02 (m, 2H), 3.02-2.90 (m, 2H), 1.51-1.30 (m, 18H). $^{13}$C NMR (75 MHz, DMSO): 156.2, 155.6, 145.8, 136.5, 132.6, 129.1, 127.3, 126.7, 115.0, 77.6, 72.1, 40.6, 39.3, 34.6, 28.2.

EXAMPLE 7

Synthesis of tert-butyl (2-(3-(5-amino-1-methyl-1H-pyrazol-4-yl)ureido)ethyl)carbamate

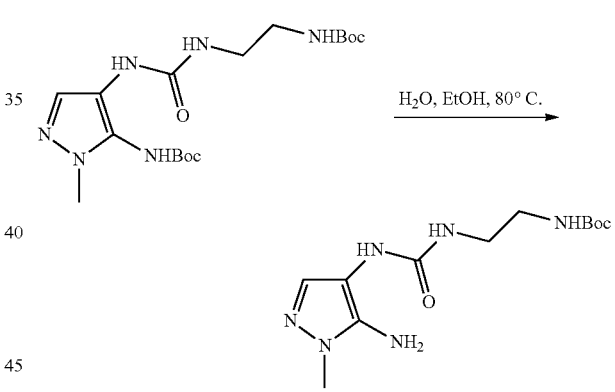

In a 3-neck round bottom flask equipped with a reflux condenser, tert-butyl (2-(3-(5-((tert-butoxycarbonyl)amino)-1-methyl-1H-pyrazol-4-yl)ureido)ethyl)carbamate prepared according to Example 5 (43.6 g, 109.5 mmol, 1 equiv) was dissolved in absolute ethanol (90 mL). To this solution, water (450 mL) was added. The resulting suspension was heated to 110° C. with vigorous stirring, whereby the suspension slowly dissolved (solid encrusted on the reaction vessel walls was washed with additional 5 mL ethanol). After a total of 5 h, HPLC control indicated 94% conversion. The reaction was cooled to 85° C., stirred for an additional 1.5 h and cooled to r.t. The crude reaction mixture was diluted with THF (450 mL), charged with 25% aq. NaCl solution (450 mL) and the phases were separated. The aqueous phase was extracted with THF (1×450 mL and 1×250 mL). The combined organic phases were evaporated under reduced pressure, the residue was redissolved in methanol (250 mL) and evaporated to dryness again. Drying at 50° C. under reduced pressure for 17 h gave the title product as white crystalline solid (26.3 g, 88.1 mmol, 81%).

Characterization Data for the Product:

$^1$H NMR (300 MHz, DMSO): 7.52 (br s, 1H), 6.98 (s, 1H), 6.81 (br s, 1H), 6.09 (br s, 1H), 4.84 (br s, 2H), 3.50 (s, 3H), 3.11-3.01 (m, 2H), 3.01-2.91 (m, 2H), 1.38 (s, 9H).

$^{13}$C NMR (75 MHz, DMSO): 156.8, 155.6, 140.2, 133.6, 103.4, 77.5, 40.6, 39.4, 34.7, 28.2.

COMPARATIVE EXAMPLE 1

Overview of Attempted Hofmann Rearrangement Using Classical Reagents

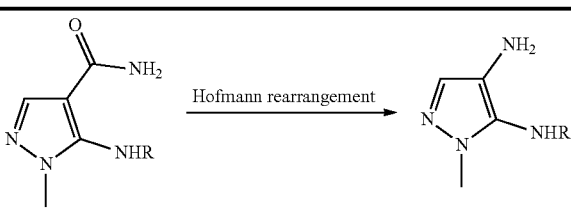

| R | Reagent | equiv | Base | equiv | Solvent | Temp, °C. | Time, h | Result |
|---|---|---|---|---|---|---|---|---|
| H | Br$_2$ | 1 | KOH | 14 | H$_2$O | −5 to 80 | 17 | 3% product + decomp. |
| H | NaOCl | 1 | NaOH | 1.9 | H$_2$O | 70 | 3.5 | educt + decomposition |
| H | NBS | 1.5 | KOH | 6 | MeOH/H$_2$O | 0 to r.t. | 5 | no conversion |
| Boc | NBS | 1.5 | DBU | 10 | 1,4-dioxane | 10 to r.t. | 1 | decomposition |
| Boc | NBS | 1.5 | KOH | 10 | 1,4-dioxane | r.t. to 65 | 1.5 | no conversion |

COMPARATIVE EXAMPLE 2

Synthesis of tert-butyl (4-amino-1-methyl-1H-pyrazol-5-yl)carbamate

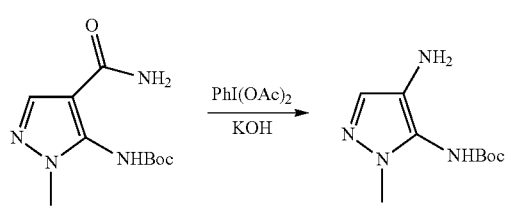 [SMILES: "PhI(OAc)2" ; Cn1ncc(C(N)=O)c1NC(=O)OC(C)(C)C ; "KOH" ; Cn1ncc(N)c1NC(=O)OC(C)(C)C]

In a two-neck round bottom flask, tert-butyl (4-carbamoyl-1-methyl-1H-pyrazol-5-yl)carbamate prepared according to Example 3 (300 mg, 1.25 mmol, 1 equiv) was dissolved in 1,4-dioxane (3 mL). To this solution was added water (0.3 mL) and 50% aq. KOH solution (930 µL, 12.5 mmol, 10 equiv). The resulting emulsion was heated to 40° C. and a solution of diacetoxyiodobenzene (603 mg, 1.87 mmol, 1.5 equiv) in 1,4-dioxane (3 mL) and water (0.3 mL) was added dropwise over 30 min. The reaction was stirred for 1 h at 40° C. and a second portion of diacetoxyiodobenzene (80 mg, 0.25 mmol, 0.2 equiv) was added in one portion. The reaction was stirred for 3 h at 40° C., cooled to r.t and diluted with dichloromethane (30 mL). The pH was adjusted to 8.5 with 50% aq. H$_2$SO$_4$ solution, resulting in phase separation. The phases were separated and the aqueous phase washed with dichloromethane (20 mL). The combined organic phases were dried over Na$_2$SO$_4$, filtered and evaporated under reduced pressure. Drying at 40° C. under high vacuum for 17 h gave the title product as pale brown gum which solidified upon standing (127 mg, 0.60 mmol, 48%).

Characterization Data for the Product:

$^1$H NMR (300 MHz, CDCl$_3$): 7.13 (s, 1H), 6.44 (br s, 1H), 3.66 (s, 3H), 3.19 (br s, 2H), 1.50 (s, 9H).

COMPARATIVE EXAMPLE 3

Synthesis of tert-butyl methyl (1-methyl-1H-pyrazole-4,5-diyl)dicarbamate

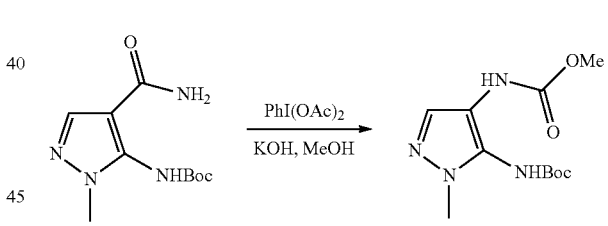

In a two-neck round bottom flask, tert-butyl (4-carbamoyl-1-methyl-1H-pyrazol-5-yl)carbamate prepared according to Example 3 (1 g, 4.16 mmol, 1 equiv) was suspended in methanol (10 mL) and charged with water (1 mL). The resulting clear solution was cooled to 0° C. and charged with 50% aq. KOH solution (3.1 mL, 41.6 mmol, 10 equiv) (caution: exothermic). Diacetoxyiodobenzene (2.01 g, 6.24 mmol, 1.5 equiv) was added in one portion (caution: exothermic). The resulting grey suspension was stirred at 0° C. for 10 min and the cooling was removed, whereby a red solution was formed. After 1 h, HPLC control indicated complete conversion of the starting material and the reaction was diluted with EtOAc (50 mL). The crude reaction mixture was extracted with sat. aq. NaHCO$_3$ (50 mL), the aqueous phase was washed with EtOAc (25 mL) and the combined organic phases were tried over Na$_2$SO$_4$, filtered and evaporated under reduced pressure. Drying at 30° C. under reduced pressure for 48 h gave the title product as off-white crystalline solid (571 mg, 2.11 mmol, 51%).

Characterization Data for the Product:

$^1$H NMR (300 MHz, DMSO): 7.44 (s, 1H), 6.65 (br s, 1H), 6.49 (br s, 1H), 3.78 (s, 3H), 3.73 (s, 3H), 1.5 (s, 9H).

$^{13}$C NMR (75 MHz, DMSO): 154.5, 153.0, 131.3, 127.1, 114.4, 79.6, 51.6, 35.6, 27.9.

The invention claimed is:

1. Process for production of a compound of formula

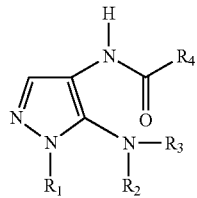

I wherein $R_1$ is H, straight or branched $C_1$-$C_6$ alkyl, optionally substituted by 1 to 5 hydroxy groups which may be protected or halogen atoms, $R_2$ is H, straight or branched $C_1$-$C_6$ alkyl or an amino protecting group, or $R_1$ and $R_2$ are bonded together to form $C_1$-$C_6$ alkylene or $C_2$-$C_6$ alkenylene, $R_3$ is H, straight or branched $C_1$-$C_6$ alkyl or an amino protecting group, wherein $R_3$ is not H if $R_2$ is H, $R_4$ is

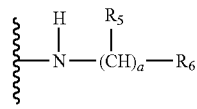

wherein a is 0, 1, 2, 3, 4, 5 or 6, $R_5$ is H or hydroxy which may be protected, and $R_6$ is H, $C_1$-$C_6$ straight or branched alkyl, mono or di straight or branched $C_1$-$C_6$ alkylamino, $C_3$-$C_6$ cycloalkyl, $C_3$-$C_6$ cycloalkyl amino, $C_6$-$C_{12}$ aryl, $C_6$-$C_{12}$ aryl amino, protected amino, protected guanidino or a saturated 3- to 8-membered heterocyclic group containing 1 to 4 nitrogen atoms, wherein the cycloalkyl or aryl is optionally substituted by one or more $C_1$-$C_3$ straight or branched alkyl and the heterocyclic group is optionally substituted by one or more protected amino groups comprising reacting a compound of formula

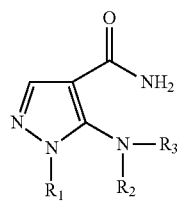

II wherein $R_1$, $R_2$ and $R_3$ are as defined above with a compound of formula

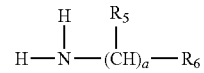

III wherein a, $R_5$ and $R_6$ are as defined above and PhI(OAc)$_2$ in the presence of a non-nucleophilic base to produce the compound of formula I.

2. The process according to claim 1, wherein $R_1$ is straight or branched $C_1$-$C_6$ alkyl.

3. The process according to claim 1, wherein $R_2$ is an amino protecting group.

4. The process according to claim 1, wherein $R_3$ is H.

5. The process according to claim 1, wherein $R_4$ is

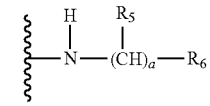

wherein a is 0, 1, 2, 3, 4, 5 or 6, $R_5$ is H or hydroxy which may be protected, and $R_6$ is H, mono or di straight or branched $C_1$-$C_6$ alkylamino or straight or branched $C_1$-$C_6$ alkoxycarbonylamino.

6. The process according to claim 1, wherein $R_4$ is

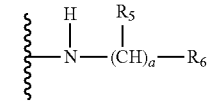

wherein a is 1, 2, or 3, $R_5$ is H, and $R_6$ is straight or branched $C_1$-$C_6$ alkoxycarbonylamino.

7. The process according to claim 1, wherein $R_1$ is methyl, $R_2$ is an amino protecting group, $R_3$ is H, and $R_4$ is

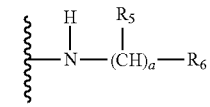

wherein a is 2, $R_5$ is H, and $R_6$ is protected amino.

8. The process according to claim 1, wherein $R_1$ is methyl, $R_2$ is Boc or trityl, $R_3$ is H, and $R_4$ is

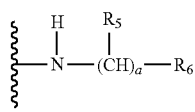

wherein a is 2,
$R_5$ is H, and
$R_6$ is NH-Boc.

9. The process according to claim 1, wherein the non-nucleophilic base is 1,8-diazabicycloundec-7-ene.

10. The process according to claim 1, wherein production of the compound of formula I is conducted in a non-nucleophilic solvent.

11. The process according to claim 1, wherein production of the compound of formula I is conducted under anhydrous conditions.

12. The process according to claim 1, wherein the compounds of formula II and formula III are used in a molar ratio of 1/1.2 to 1/3.

13. The process according to claim 1, wherein the compound of formula II and PhI(OAc)$_2$ are used in a molar ratio of 1/1.1 to 1/1.9.

14. The process according to claim 1, wherein the compound of formula II is prepared by a process of converting a compound of formula

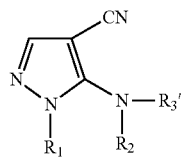

IV wherein $R_1$ and $R_2$ are as defined in claim 1, and $R_{3'}$ is straight or branched $C_1$-$C_6$ alkyl or an amino protecting group
into the compound of formula II.

15. A process for preparation of Ceftolozane or a salt thereof which comprises
a) preparing a compound of formula I by the process according to claim 1 wherein $R_1$ is methyl, $R_2$ is H or an amino protecting group, $R_3$ is an amino protecting group, and
$R_4$ is

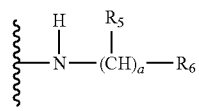

wherein a is 2,
$R_5$ is H,
and $R_6$ is protected amino, b) reacting the compound of formula I, optionally after deprotection, with at least one other intermediate product and removing any remaining protection group to obtain Ceftolozane or salt thereof.

* * * * *